US011719250B2

(12) United States Patent
Li (10) Patent No.: US 11,719,250 B2
(45) Date of Patent: Aug. 8, 2023

(54) NECK FAN

(71) Applicant: Shenzhen Jisu Technology Co., Ltd, Shenzhen (CN)

(72) Inventor: Xiangfu Li, Shenzhen (CN)

(73) Assignee: SHENZHEN JISU TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 17/585,594

(22) Filed: Jan. 27, 2022

(65) Prior Publication Data
US 2022/0145896 A1    May 12, 2022

Related U.S. Application Data

(63) Continuation of application No. 17/471,178, filed on Sep. 10, 2021, which is a continuation of application No. PCT/CN2020/128564, filed on Nov. 13, 2020.

(30) Foreign Application Priority Data

Oct. 25, 2019   (CN) .......................... 201921815938.3
Sep. 30, 2020   (CN) .......................... 202022210032.8

(51) Int. Cl.
*F04D 25/16*    (2006.01)
*A61F 7/00*    (2006.01)
(Continued)

(52) U.S. Cl.
CPC ....... *F04D 25/166* (2013.01); *F04D 29/4213* (2013.01); *F04D 29/4246* (2013.01);
(Continued)

(58) Field of Classification Search
CPC ............... F04D 29/424; F04D 29/4226; F04D 29/4246; F04D 25/084; F04D 25/08;
(Continued)

(56) References Cited

U.S. PATENT DOCUMENTS 5,802,865 A * 9/1998 Strauss ..................... A61F 7/10
                                                            62/259.3
6,682,552 B2 * 1/2004 Ramsden .................. A61F 7/10
                                                            607/114
(Continued)

FOREIGN PATENT DOCUMENTS

CN    202001342 U   † 10/2011
CN    211059041    * 10/2019   ............. F04D 25/08
(Continued)

OTHER PUBLICATIONS

International search report, International Application No. PCT/CN2020/128564, dated Jun. 24, 2021 (16 pages).
(Continued)

*Primary Examiner* — Eldon T Brockman
*Assistant Examiner* — Andrew J Marien (57) ABSTRACT

A neck fan includes an arc-shaped shell configured to hang around user's neck and at least four fan assemblies arranged in the shell. The shell includes a first part and a second part. Each of the first part and the second part defines an accommodating space, air inlets and air outlets communicated with the accommodating space, at least one partition is arranged in the accommodating space and configured to divide the accommodating space into at least two accommodating parts arranged along an extension direction of the shell. Each of the fan assemblies is arranged in one of the at least two accommodating parts and is configured to direct air into the one of the at least two accommodating parts through corresponding air inlets and to direct air out of the one of the at least two accommodating parts through corresponding air outlets.

19 Claims, 6 Drawing Sheets

(51) Int. Cl.
*F04D 29/42* (2006.01)
*F04D 25/06* (2006.01)
*F04D 29/00* (2006.01)

(52) U.S. Cl.
CPC ............... *A61F 2007/0011* (2013.01); *A61F 2007/0067* (2013.01); *F04D 25/0673* (2013.01); *F04D 29/005* (2013.01)

(58) Field of Classification Search
CPC ............... F04D 25/166; A41D 20/005; A61F 2007/20009; A61F 2007/001; A61F 2007/0011; A42B 3/286; F24F 2221/38; F24F 7/007
See application file for complete search history.

(56) References Cited

U.S. PATENT DOCUMENTS

| | | | |
|---|---|---|---|
| 10,709,601 | B2 * | 7/2020 | Adair ............... A61F 7/02 |
| 11,187,241 | B1 * | 11/2021 | Liu ............... F04D 29/441 |
| 2011/0240026 | A1 | 10/2011 | Ausen |
| 2011/0259028 | A1 | 10/2011 | Lee |
| 2015/0374046 | A1 | 12/2015 | Peavy et al. |
| 2017/0266038 | A1 * | 9/2017 | Peavy ............... A41D 13/0053 |
| 2017/0370596 | A1 * | 12/2017 | Lee ............... F04D 25/084 |
| 2019/0234412 | A1 | 8/2019 | Schwimmer et al. |
| 2020/0187574 | A1 * | 6/2020 | Te Hsiang ......... A41D 13/0053 |
| 2020/0240438 | A1 | 7/2020 | Ma et al. |
| 2021/0310718 | A1 | 10/2021 | Zeng et al. |
| 2021/0355959 | A1 † | 11/2021 | Liu |
| 2021/0355963 | A1 | 11/2021 | Kang |
| 2022/0235786 | A1 | 7/2022 | Liu et al. |

FOREIGN PATENT DOCUMENTS

| | | | |
|---|---|---|---|
| CN | 210623163 | U | 5/2020 |
| CN | 210829801 | U | 6/2020 |
| CN | 211059041 | U | 7/2020 |
| CN | 211116729 | U | 7/2020 |
| CN | 211116731 | U | 7/2020 |
| CN | 211314612 | U | 8/2020 |
| CN | 211692914 | U | 10/2020 |
| CN | 212536129 | U | 2/2021 |
| CN | 212536145 | U | 2/2021 |
| CN | 212563735 | U | 2/2021 |
| CN | 212615494 | U | 2/2021 |
| CN | 212615499 | U | 2/2021 |
| CN | 212615505 | U | 2/2021 |
| CN | 212690406 | U | 3/2021 |
| CN | 212867975 | U | 4/2021 |
| CN | 212899050 | U | 4/2021 |
| CN | 213206044 | U | 5/2021 |
| CN | 213206107 | U | 5/2021 |
| CN | 213392779 | U | 6/2021 |
| CN | 213392786 | U | 6/2021 |
| CN | 213392811 | U | 6/2021 |
| CN | 213450914 | U | 6/2021 |
| CN | 213450915 | U | 6/2021 |
| CN | 213684600 | U | 7/2021 |
| CN | 215566774 | U | 1/2022 |
| CN | 215719690 | U | 2/2022 |
| CN | 215719696 | U | 2/2022 |
| CN | 215860859 | U | 2/2022 |
| CN | 215908080 | U | 2/2022 |
| CN | 215927841 | U | 3/2022 |
| JP | 3220810 | U | 4/2019 |
| JP | 3230942 | U | 3/2021 |

OTHER PUBLICATIONS

Non Final Office Action, U.S. Appl. No. 17/741,178, dated Mar. 29, 2022 (25 pages).
Final Office Action, U.S. Appl. No. 171471,178, dated Jun. 2, 2022 (17 pages).
Non Final Office Action, U.S. Appl. No. 17/717,139, dated Jun. 22, 2022 (29 pages).
Non Final Office Action, U.S. Appl. No. 17/717,131, dated Jun. 24, 2022 (29 pages).
International search report and Written Opinion of the International Search Authority, International Application No. PCT/CN2022/086120, dated Jul. 15, 2022 (16 pages).
Advisory Office Action, U.S. Appl. No. 17/717,131, dated Dec. 22, 2022 (9 pages).
Advisory Office Action, U.S. Appl. No. 17/717,131, dated Feb. 2, 2023 (7 pages).
Advisory Office Action, U.S. Appl. No. 17/717,139, dated Jan. 11, 2023 (18 pages).
Advisory Office Action, U.S. Appl. No. 17/717,139, dated Mar. 1, 2023 (5 pages).
Japanese Decision of Refusal, Japanese Patent Application No. 2022-514282, dated Feb. 7, 2023 (4 pages).
Final Office Action, U.S. Appl. No. 17/739,081, dated Mar. 7, 2023 (33 pages).
Final Office Action, U.S. Appl. No. 17/471,178, dated Dec. 13, 2022 (44 pages).
Non Final Office Action, U.S. Appl. No. 17/739,081, dated Sep. 22, 2022 (126 pages).

\* cited by examiner
† cited by third party

NECK FAN

CROSS-REFERENCE TO RELATED APPLICATIONS

This is a continuation of U.S. patent application Ser. No. 17/471,178 filed on Sep. 10, 2021, which is a continuation of International Application No. PCT/CN2020/128564 filed on Nov. 13, 2020 under 35 U.S.C. § 371. The present application claims the priority of Chinese patent application No. 201921815938.3 filed on Oct. 25, 2019, and the International Application claims the priority of Chinese patent application No. 202022210032.8, filed on Sep. 30, 2020. Both applications are incorporated herein by reference in their entireties.

FIELD

The subject matter herein generally relates to fans, and particularly relates to a fan hanging around a neck.

BACKGROUND

In recent years, people are increasingly pursuing a more convenient life. In order to meet needs of practical fans for outdoor activities or other life scenes, there are a variety of portable fans in the market, such as neck fans. The emergence of neck fans solves limited activity due to handheld fans. The neck fan can free users' hands and realize cooling anytime and anywhere without holding it, whether during sports, outdoor activities or in office.

Existing neck fan generally has a fan assembly with two fan blades exposed at both ends of the neck fan. Such fan assembly not only has low safety that hair is easy to get involved in the fan blades, but also has problems such as outputted air being uncomfortable due to too concentrated air outlets, which needs to be improved.

SUMMARY OF THE INVENTION

In a first aspect, a neck fan includes an arc-shaped shell and at least two fan assemblies. The arc-shaped shell is configured to be worn around a neck of a user. The arc-shaped shell comprises a first portion configured to be worn around a side of the neck and a second portion configured to be worn around another side of the neck. Each of the first portion and the second portion includes a wall defining a receiving space, and the wall comprises a first side wall close to the neck and a second side wall connected to and opposite to the first side wall. Each of the first side wall and the second side wall defines a plurality of air inlets, at least one of the first side wall and the second side wall defines a plurality of air outlets, and the plurality of air inlets and the plurality of air outlets are communicating with the receiving space. At least two fan assemblies are received in the receiving space of the first portion and the receiving space of the second portion, wherein each of the at least two fan assemblies is configured to guide air from the plurality of air inlets of the first side wall and the second side wall of a respective portion to the plurality of air outlets of the respective portion.

In a second aspect, a neck fan includes an arc-shaped shell, at least one partition, and at least two fan assemblies. The arc-shaped shell is configured to be worn around a neck of a user. The arc-shaped shell comprises a first portion configured to be worn around a side of the neck and a second portion configured to be worn around another side of the neck. Each of the first portion and the second portion comprises a wall, the wall defines a receiving space, a plurality of air inlets communicating with the receiving space, and a plurality of air outlets communicating with the receiving space. At least one partition is received in the receiving space and dividing the receiving space into at least two receiving sub-spaces, wherein the at least two receiving sub-spaces are distributed along an extension direction of the arc-shaped shell. The least two fan assemblies are received in the at least two receiving sub-spaces respectively and configured to guide air to flow from the plurality of air inlets to the plurality of air outlets. The at least one partition and the wall cooperatively define an air duct. A cross-sectional area of the air duct is gradually decreased along a direction from the first portion to the second portion, and/or a cross-sectional area of the air duct of the second portion is gradually decreased along a direction from the second portion to the first portion.

In a third aspect, a turbine blade assembly for a neck fan is provided. The turbine blade assembly has a first side and a second side opposite to the first side. The turbine blade assembly comprises a first side blade disposed at the first side, a second side blade disposed at the second side, and a separation plate disposed between the first side and the second side. The first side defines a first inlet window, the second side defines a second inlet window. The first inlet window and the second inlet window are defined to allow air to flow in from an outside of the neck fan.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the invention, "a plurality of" means two or more, unless otherwise specifically defined.

Figure 1:
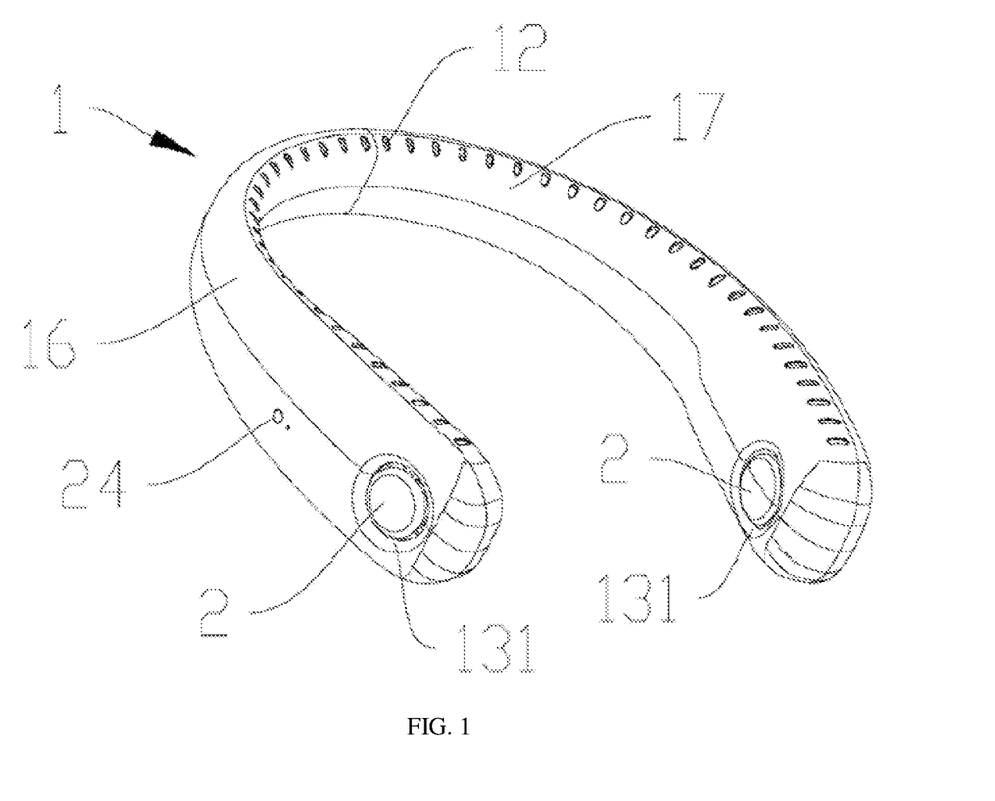
FIG. 1 is a schematic view of a neck fan according to an embodiment of the present application.
Figure 2:
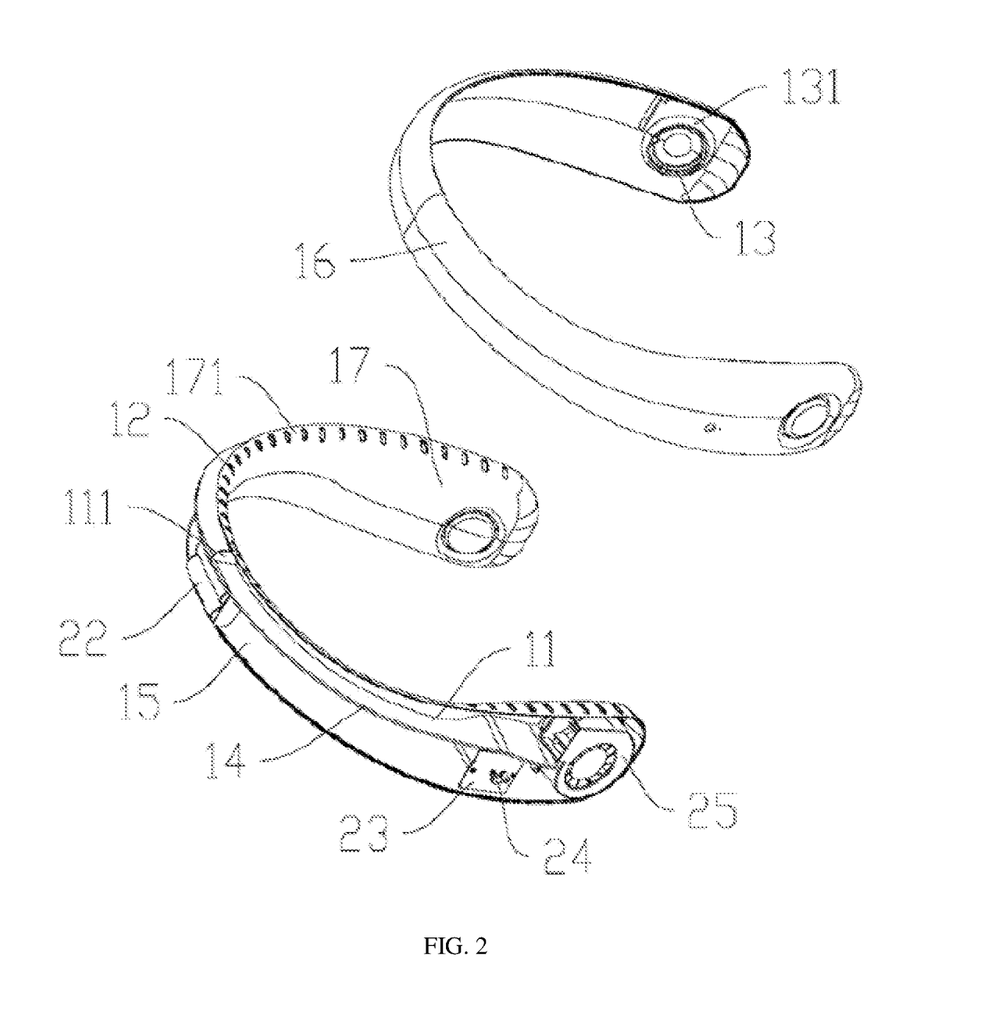
FIG. 2 is an explosive view of a neck fan according to an embodiment of the present application.

In an embodiment, as shown in FIGS. 1 and 2, the present disclosure provides a neck fan including a body portion 1 and a fan assembly 2. The body portion 1 may be worn around a neck of a user. The body portion 1 defines an air duct 11. The body portion 1 defines a plurality of air outlets 12 communicating with the an outside of the neck fan and the air duct 11. In this way, air in the air duct 11 may flow to the outside through the air outlets 12. The fan assembly 2 is mounted on the body portion 1 and is configured to drive the air from the outside into the air duct 11 and blow the air to the outside through the air outlets 12. The air driven into the air duct 11 through fan assembly 2 has a certain speed. Therefore, a wind pressure difference is present between an inside and the outside of air outlets 12, i.e., between the air duct and the outside. In this case, while the air is being blown to the outside through the air outlets 12, due to the wind pressure difference, some of the air in the air duct 11 may flow out of the air duct 11 through air outlets 12 to reach the neck to cool the user. In an embodiment, the plurality of air outlets 12 are evenly distributed and spaced apart from each other. Therefore, when being worn, the body portion 1 surrounds a front, a side and a back of the neck, and the air blown out from the air outlets 12 may be directed to the front, the side and the back of the neck. In this way, a range that the air may reach is expanded, and the user may be cooled from various directions. The neck fan is highly applicable and may be used conveniently.

As shown in FIG. 1, the body portion 1 may be bent and tubular and may be made of an elastic material that can be extended and retracted. When putting on the body portion, two ends of the body portion 1 may be pulled apart from each other to form a gap, and a size of the gap may be greater than a size (such as a diameter) of the neck. After the neck fan is worn to the neck, the body portion may be reset, i.e., the two ends may be reset to original positions, and the gap between the two ends of the body portion may be reduced. In some embodiments, when the two ends are at the original positions, the two ends may be spaced apart from each other, and a size of the gap therebetween may be less than the size of the neck. In some embodiments, when the two ends of the body portion are at the original positions, the two ends may be connected to each other, such that the body portion is ring-shaped (such as forming an enclosed circle). The body portion 1 may be made of plastic. The user may carry the body portion easily and may feel comfortable when wearing the body portion. The air outlets 12 are oriented towards an inside and/or a top of the bent and tubular body portion. Therefore, while being worn, the neck does not cover the air outlets 12, allowing the air to be blown out the air outlets 12 to the neck smoothly. In detail, some of the air outlets 12 defined in the body portion 1 are oriented towards the inside of the tubular body portion, and some of the air outlets 12 are oriented towards the top of the tubular body portion 1, increasing a range covered by the air supplied from the air outlets 12.

Figure 3:
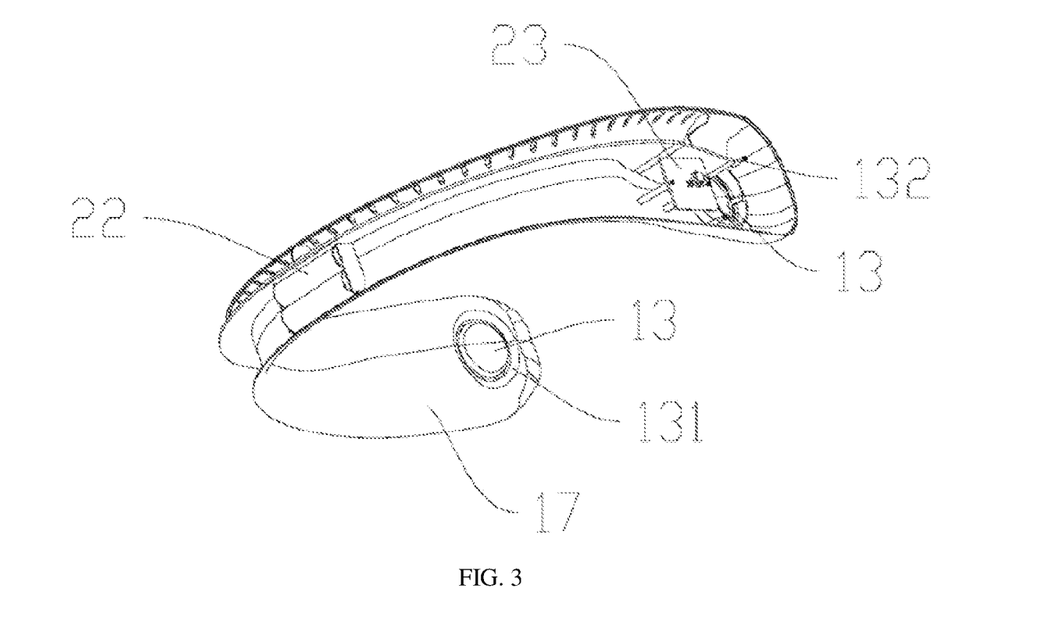
FIG. 3 is a schematic view of an inner shell of a neck fan according to an embodiment of the present application.

As shown in FIGS. 1 to 3, each of two ends of the body portion 1 defines a mounting cavity 13. The fan assembly 2 is received in the mounting cavity 13 to be mounted with the body portion 1. A portion of the body portion 1 corresponding to the mounting cavity 13 defines an air inlet 131. The fan assembly 2 is fixedly received in the mounting cavity 13. When the fan assembly 2 is operating, the fan assembly 2 draws in the air in the outside through the air inlet 131, and is configured to accelerate the air to drive the air to flow into the air duct 11. In the present embodiment, two ends of the body portion 1 define two mounting cavities 13, and two fan assemblies 2 may be received in the two mounting cavities 13, respectively. Each of the two fan assemblies 2 may operate independently. A plate 111 may be arranged in a middle of the air duct 11 to divide the air duct 11 into two sections. One of the two sections of the air duct 11 corresponds to one of the two fan assemblies 2. By arranging the plate 111, a length of the air duct 11 may be reduced effectively, ensuring an air velocity at an air outlet 12, which is further away from the fan assembly 2.

Figure 4:
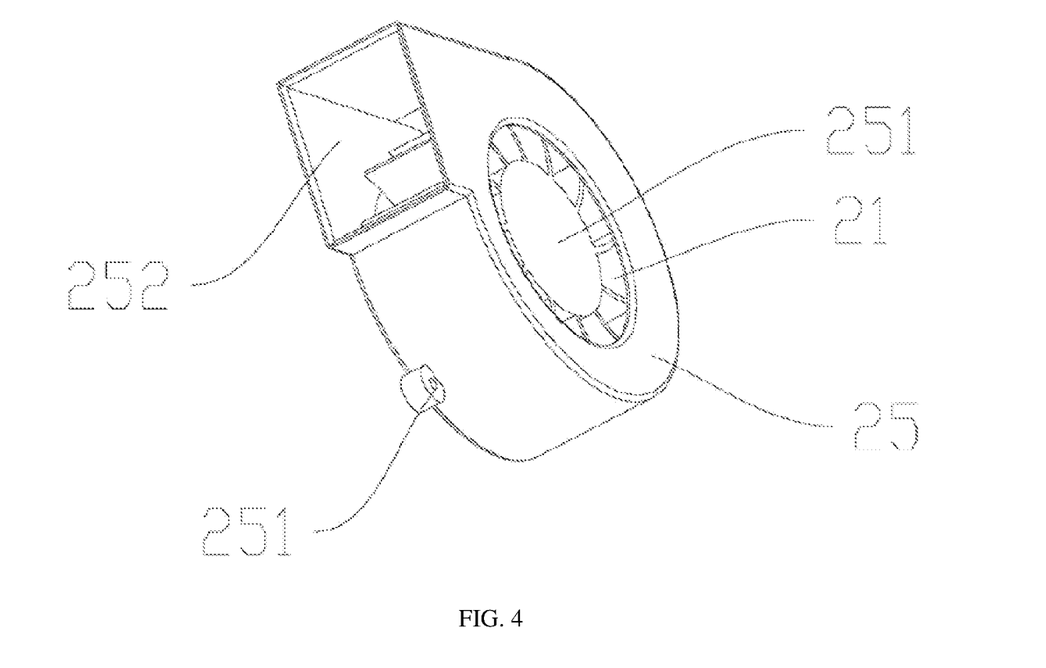
FIG. 4 is a schematic view of a turbo fan of a neck fan according to an embodiment of the present application.

As shown in FIGS. 2 and 4, the fan assembly 2 includes a fan blade 21, a motor (not shown in the figures) which drives the fan blade 21 to rotate to generate an air flow, a battery 22 which provides power to the motor, a main control circuit board 23 which controls a rotation speed of the motor, and a gear switch 24 electrically connected to the main control circuit board 23. When the neck fan needs to be initiated, the gear switch 24 may be pressed, and the main control circuit board 23 may receive a signal from the gear switch 24. After receiving the signal, the main control circuit board 23 controls the motor to rotate to drive the fan blade 21 to rotate. Rotation of the fan blade 21 may lead the air at the outside to flow into the fan assembly 2 under the wind pressure, and the air may be guided by the fan assembly 2 to flow into the air duct 11. When the wind speed of the air flowing out of the air outlets 12 needs to be adjusted, the gear switch 24 may be pressed to generate various gear signals. The main control circuit board 23 may receive the gear signals and control the rotation speed of the motor to further control the rotation speed of the fan blade 21 connected to the motor. Accordingly, a speed of the air driven by the fan assembly 2 to flow into the air duct 11 and a speed of the air flowing out through the air outlets 12 may change. A partition 14 may be arranged inside the body portion 1. The partition 14 separates an inner space of the body portion 1 into a shaped cavity 15 and the air duct 11. The battery 22 and the circuit board both are received in the shaped cavity 15. The battery 22 may be disposed in a middle of the inner space of the body portion 1. In this way, the fan assemblies 2 are arranged at the two ends of body portion 1, whereas the battery 2 is arranged at the middle of the body portion 1, the two ends of the body portion 1 may not be too heavy, and weights of the two ends of the body portion 1 may be balanced, preventing a weight center of the body portion 1 from being shifted towards one side.

As shown in FIG. 2, a cross-sectional area of the air duct 11 gradually decreases from the two ends to the middle of the body portion 1. The air flowing from the two ends to the middle of the body portion 1 may generate a frictional force. At the same time, the cross-sectional area of the air duct 11 decreases from the two ends to the middle of the body portion 1, i.e., the cross-sectional area that the air passes through while flowing in the air duct 11 decreases. In this way, an effect of the frictional force on slowing down the speed of the air flow in the air duct 11 may be partially or completely eliminated. The speed of the air flowing out of the air outlets 12 may be controlled within a certain range, solving a problem of a large difference between the speed of the air flowing out of an air outlet 12 at or near the two ends of the air duct 11 and the speed of the air flowing out of an air outlet 12 in the middle of the air duct 11.

As shown in FIG. 2, the body portion 1 includes an outer shell 16 and an inner shell 17. Compared to the body portion 1 configured as a one-piece structure, the body portion 1 of the present embodiment is assembled from the outer shell 16 and the inner shell 17, allowing the fan assemblies to be processed and assembled more simply, and allowing later maintenance to be performed more easily. The partition 14 is arranged on the inner shell 17 and extends towards the outer shell 16. The air duct 11 is defined cooperatively by the inner shell 17, the outer shell 16 and the partition 14. When the outer shell 16 is connected to the inner shell 17, the partition 14 tightly abuts against an inner side of the outer shell 16, preventing the air in the air duct 11 from entering the shaped cavity 15. The air outlets 12 are defined in the inner shell 17. A portion of the inner shell 17 that contacts the neck of the user extending upwardly to form a curved surface 171. The curved surface 171 may be inclined at a certain angle relative to the portion that contacts the neck of the user, and the air outlets 12 are defined in the curved surface 171, such that the air outlets 12 are oriented towards the inner side of the tubular body portion.

As shown in FIGS. 2 and 4, the fan assembly 2 includes a turbine fan 25. The turbine fan 25 defines two inlet windows 251, increasing a circulation area and an efficiency of the turbine fan 25 communicating with the external air. A cavity wall of the mounting cavity 13 defines two air inlets 131 corresponding to the two inlet windows 251 of the turbine fan 25. When the turbine fan 25 is rotating, the external air may enter the inlet windows 251 through the air inlets 131. A guide post 132 is arranged on the cavity wall of the mounting cavity 13 and extends towards the turbine fan 25. The turbine fan 25 defines a guide hole 251 corresponding to the guide post 132. When the turbine fan 25 is received in the mounting cavity 13, the guide post 132 extends into the guide hole 251, thereby securing the turbine fan 25 in the mounting cavity 13.

As shown in FIG. 4, the turbine fan 25 defines an air outlet port 252, which is corresponding to and communicating with the air duct 11. An air flow generated by the turbine fan 25 enters the air duct 11 through the air outlet port 252. A portion of a wall of the air outlet port 252 is received in the air duct 11. The portion of the wall of the air outlet port 252 tightly abuts against a wall of the air duct 11, reducing a loss of the air flow generated by the turbine fan 25 while the air is being guided into the air duct 11.

Figure 5:
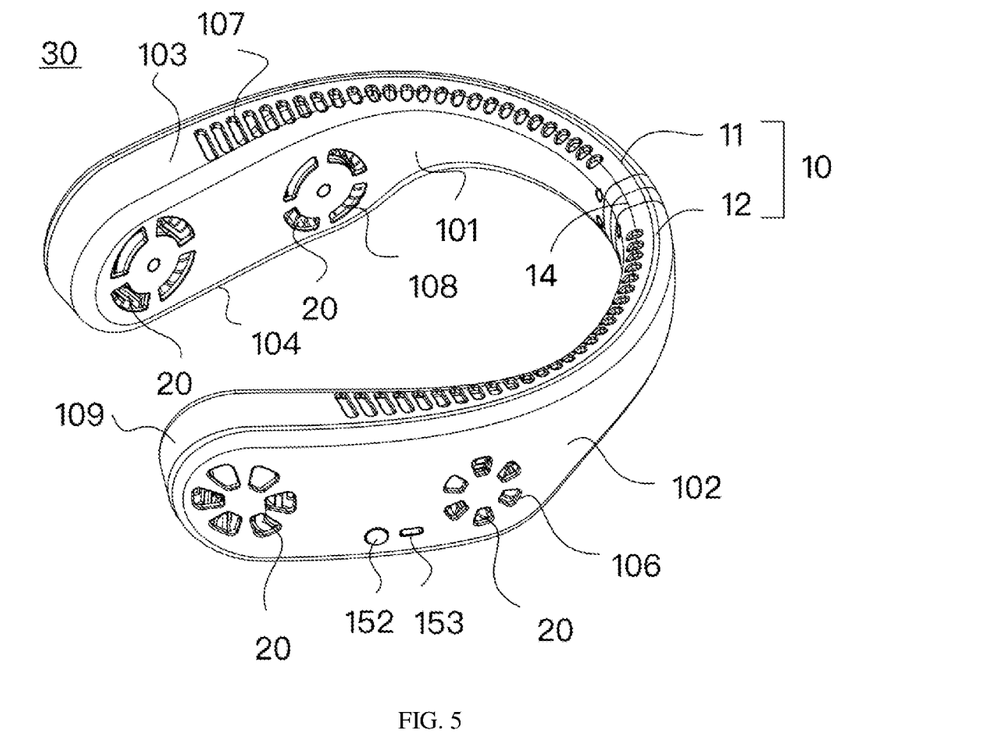
FIG. 5 is a schematic view of a neck fan in according to a first embodiment of the present disclosure.
Figure 6:
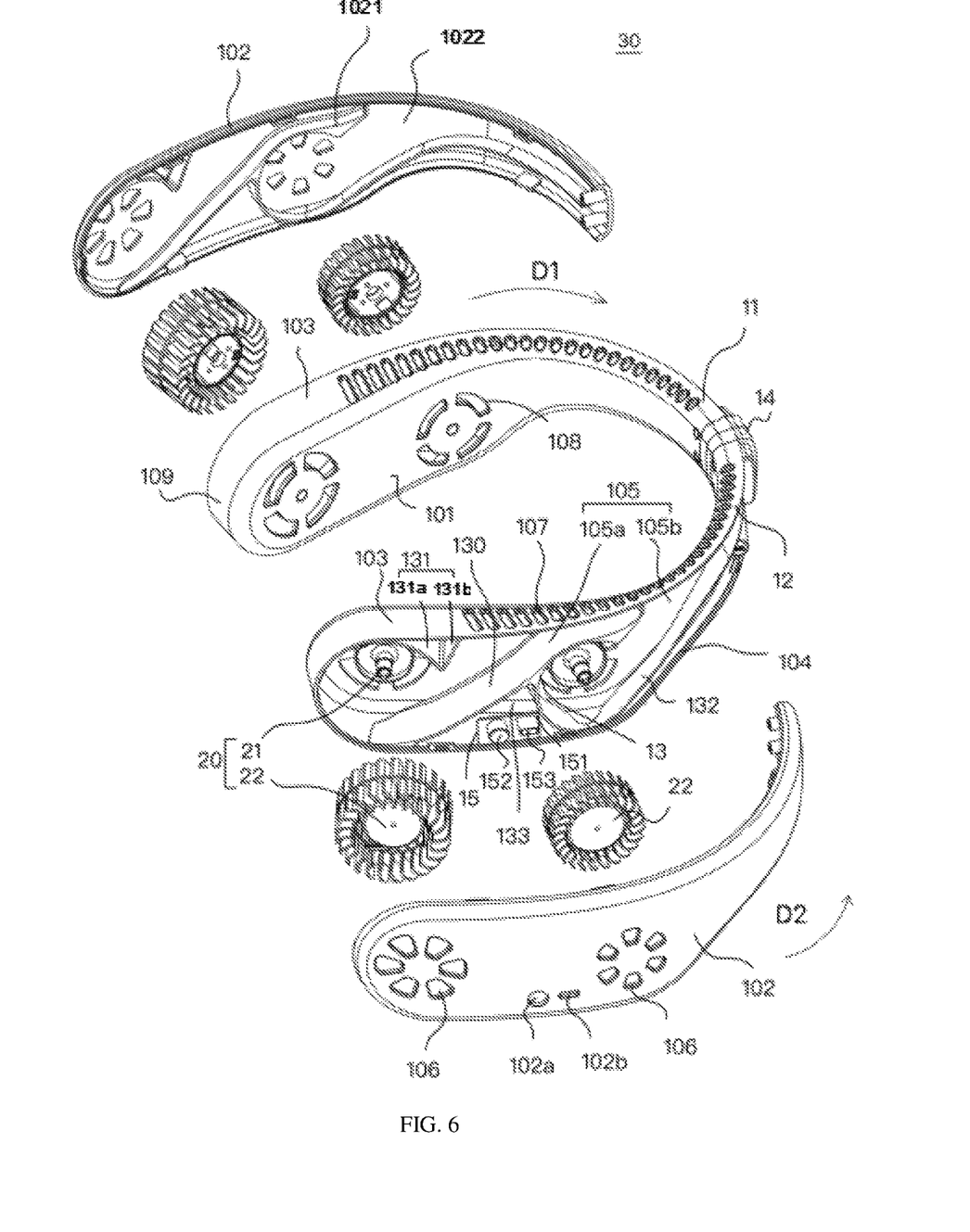
FIG. 6 is an exploded view of the neck fan of FIG. 5.

In an embodiment, as shown in FIGS. 5 and 6, FIG. 5 is a schematic view of a neck fan according to an embodiment of the present disclosure, and FIG. 6 is an explosive view of the neck fan of FIG. 5. The neck fan 30 includes an arc-shaped shell 10 and at least four fan assemblies 20. The at least four fan assemblies 20 may be arranged inside the arc-shaped shell 10. It shall be understood that, for illustration purposes only, in the following embodiment, the neck fan 30 including the at least four fan assemblies 20 will be taken as an example for illustration.

The arc-shaped shell 10 may be worn to surround the neck of the user. The arc-shaped shell 10 includes a first portion 11 and a second portion 12. The first portion 11 and the second portion 12 are arranged around two sides of the neck, such as a left side and a right side. Each of the first portion 11 and the second portion 12 includes an inner wall 101 configured to be close to the neck, an outer wall 102 opposite to the inner wall 101, a top wall 103 close to a head of the user and connecting between the inner wall 101 and the outer wall 102, and a bottom wall 104 opposite to the top wall 103 and connecting between the inner wall 101 and the outer wall 102.

The inner wall 101, the outer wall 102, the top wall 103, and the bottom wall 104 cooperatively define a receiving space 105. Each of the first portion 11 and the second portion 102 defines air inlets 106 and air outlets 107 communicating with the receiving space 105. In detail, in the present embodiment, the inner wall 101, the bottom wall 104, and the top wall 103 may be connected into an integrated structure (such as, a one-piece structure) to serve as a first side wall. The outer wall 102 may serve as a second side wall opposite to the first side wall. The first side wall and the second side wall cooperatively define the receiving space 105.

At least one partition 13 is received inside the receiving space 105 to divide the receiving space 105 into at least two receiving sub-spaces 105a and 150b. The at least two receiving sub-spaces 105a and 150b are arranged successively along an extension direction of the arc-shaped shell 10. Each of the at least two receiving sub-spaces correspond to and communicate with some of the air inlets 106 and some of the air outlets 107. Each of the fan assemblies is received in one corresponding receiving sub-space. Each of the fan assemblies is configured to guide the air, which flows into the corresponding receiving sub-space through corresponding air inlets 106, to flow to air outlets 107 corresponding to the receiving sub-space, allowing the air to be blown out through the corresponding air outlets 107. The number of the air outlets 107 may be more than one. The more than one air outlets may be distributed along the extension direction of the arc-shaped shell 10. Sizes, shapes of the air outlets 107 and/or distances between every two adjacent air outlets 107 vary gradually along the extension direction of the arc-shaped shell 10.

Compared to the neck fan in the art, in the neck fan 30 illustrated in the above-mentioned embodiments, the arc-shaped shell 10 includes the first portion 11 and the second portion 12. The first portion 11 and the second portion 12 are configured to be around two opposite sides of the neck. Each of the first portion 11 and the second portion 12 defines the receiving space 105, the air inlets 106, and the air outlets 107. The air inlets 106 and the air outlets 107 communicate with the receiving space 105. Each receiving space 105 is divided into at least two receiving sub-spaces by the partition 13. Each of the fan assemblies 20 is arranged in one of the receiving sub-spaces and configured to guide the air at the air inlets 106 to flow to the air outlets 107 to be blown out. Since the fan assemblies 20 are received in the receiving space 105, foreign matters, such as hair, may not be absorbed into the fan assemblies easily, allowing the neck fan to be used safely and conveniently. In the present embodiment, four receiving sub-spaces 105a and 105b are defined along the extension direction of the arc-shaped shell 10, and four fan assemblies 20 may be arranged and received in four receiving sub-spaces respectively. Since a plurality of the receiving sub-spaces 105a and 105b are defined, a length of the air duct in each of the receiving sub-spaces may be relatively short. When the air is flowing in each of the receiving sub-spaces, a concentration of the air being output may be reduced, the user may be comfortable about the air output, wind noise may be reduced, and an air volume loss may be reduced. The applicant of the present disclosure finds that, the longer the air duct, the longer period of time that the air flows along the receiving sub-space, increasing the wind noise and the air volume loss. By dividing the receiving space 105 into the plurality of receiving sub-spaces 105a and 105b, the wind noise and the air volume loss may be reduced significantly. In addition, by determining an extension direction, sizes, shapes of the air outlets 107 and distances between two adjacent air outlets 107, the user may be more comfortable about the air output from the neck fan 30, the air may be output from the neck fan 30 more softly, improving the user's experiences.

Further, each fan assembly 20 includes a driving shaft 21 and a fan blade assembly 22 mounted on the driving shaft 21. The driving shaft 21 extends from the inner wall 101 towards the outer wall 102. In this way, a thickness of the arc-shaped shell 10 along a direction from the inner wall 101 to the outer wall 102 may be reduced, such that the user may be comfortable when wearing the neck fan.

Further, the air inlets 106 are defined in the outer wall 102, and the air outlets 107 are defined in the top wall 103. It shall be understood that, the air inlets 106 are defined in the outer wall 102, and the outer wall 102 faces outwardly (i.e., opposite to the neck of the user), and therefore, the air may enter the shell easily and smoothly. In addition, the air outlets 107 are defined in the top wall 103, and the driving shaft 21 extends from the inner wall 101 to the outer wall 102. In this way, the fan blade assemblies 20 may direct the air from the air inlets 106 to the air outlets 107 to achieve a high air guiding efficiency. Moreover, the air outlets 107 are defined in the top wall 103, such that the air may be output towards a face and the head of the user, such that the user may be cooled rapidly.

Further, an end of the driving shaft 21 is fixedly arranged on the inner wall 101. It shall be understood that, such arrangement together with the air inlets 106 defined in the outer wall 102 allows the air inlets 106 to be unblocked, achieving a better air inlet effect.

Further, each fan assembly 20 corresponds to a plurality of air inlets 106. It shall be understood that, air is guided into the fan assembly 20 through the plurality of fan inlets 106, allowing the neck fan to have a better appearance, preventing foreign matters from entering the fan assembly 20 easily, increasing usage safety.

Further, the number of the air inlets 106 corresponding to each fan assembly 20 may be the same. The air inlets 106 corresponding to each fan assembly 20 are distributed in a circular shape. It shall be understood that, such arrangement allows the neck fan to have a better appearance, and prevents foreign matters from entering the fan assembly 20 easily. A better air inlet effect may be achieved due to such arrangement and shapes of the fan assemblies 20.

Further, a plurality of air inlets 108 are defined in the inner wall 101 corresponding to each fan assembly 20. The fan assembly 20 can guide the air from the air inlets 108 to the air outlets 107. Each of the plurality of air inlets 108 is arc shaped. The plurality of air inlets 108 corresponding to each fan assembly 20 are distributed in a circular shape. It shall be understood that, such arrangement allows the neck fan to have a better appearance, and prevents foreign matters from entering the fan assembly 20 easily. A better air inlet effect may be achieved due to such arrangement and shapes of the fan assemblies 20.

Further, the fan blade assembly 22 is a turbine fan blade assembly. It shall be understood that the turbine fan blade assembly may reduce the wind noise and improves the usage safety.

Further, the neck fan 30 further includes a connecting portion 14 connected between the first portion 11 and the second portion 12. The connecting portion 14 is configured to join the first portion 11 and the second portion 12 into an integrated structure. In the present embodiment, the connecting portion 14 may be configured as an individual element. In some embodiments, the connecting portion 14 may be integrally formed with one of the first portion 11 and the second portion 12, and then assembled with the other of the first portion 11 and the second portion 12. A structure of the connecting portion 14 may be various, and shall not be limited by the present disclosure.

The first portion 11 further includes an end plate 109 disposed at an end of the first portion 11 away from the connecting portion 14. The second portion 12 further includes an end plate 109 disposed at an end of the second portion 12 away from the connecting portion 14. Each end plate 109 is connected to the top wall 103, the bottom wall 104, the inner wall 101 and the outer wall 102. Sizes of the air inlets 106 corresponding to the fan assembly 20 arranged near the connecting portion 14 are less than those of the air inlets 106 corresponding to the fan assembly 20 arranged near the end plate 109. An outer diameter of the fan assembly 20 arranged near the connecting portion 14 is less that that of the fan assembly 20 arranged near the end plate 109. In other words, an end of the first portion 11 at which the end plate 109 is disposed may serve as a free end, and an end of the second portion 12 at which the end plate 109 is disposed may serve as another free end. An end of the first portion 11 near the connecting portion 14 may serve as a connecting end, and an end of the second portion 12 near the connecting portion 14 may serve as another connecting end. In the present embodiment, the sizes of the air inlets 106 corresponding to the fan assembly 20 arranged near the connecting end are less than those of the air inlets 106 corresponding to the fan assembly 20 arranged near the free end. The outer diameter of the fan assembly 20 arranged near the connecting end is less than that of the fan assembly 20 arranged near the free end. It shall be understood that, by determining various sizes of the air inlets 106 and various outer diameters of the fan blade assemblies 20, a size of the arc-shaped shell 10 may be gradually reduced along a direction from the end plate 109 to the connecting portion 14, such that the shell 10 is more suitable to a curve of the neck, allowing the user to be comfortable. In the present embodiment, the end plate 109 may be arc shaped, providing a better appearance. The shape of the end plate 109 may further be suitable to shapes of the receiving sub-spaces 105a and shapes of the fan assemblies 20 to achieve a better air inlet and outlet effect.

It shall be understood that, for each of the first portion 11 or the second portion 12, the inner wall 101, the top wall 103, the bottom wall 104, the end plate 109, and the partition 13 may be formed as a one-piece structure. The outer wall 102 may be buckled with the top wall 103, the bottom wall 104, and the end plate 109 through a buckle. There may be various types of buckles and various means to connect the above structure integrally, which will not be limited by the present disclosure.

Further, the number of the air outlets 107 may be more than one. The more than one air outlets 107 are distributed along the extension direction of the arc-shaped shell 10 and extends to a position near the connecting portion 14. Sizes of the more than one air outlets 107 gradually decrease along a direction from the end plate 109 to the connecting portion 14. It shall be understood that, the more than one air outlets 107 may improve the usage safety. Sizes of the more than one air outlets 107 gradually decrease along the direction from the end plate 109 to the connecting portion 14, allowing the air to be output in a more concentrated manner, improving air outlet intensity. In addition, sizes of the receiving sub-spaces 105a and 105b gradually decrease along the extension direction of the air duct. Therefore, the air output from the overall neck fan may be more uniform, and the user may feel comfortable. In detail, the extension direction of the arc-shaped shell 10 includes a first extension direction and a second extension direction. A direction extending from the first portion 11 to the second portion 12 may be referred to as a first extension direction D1. The sizes of the more than one air outlets 107 defined in the first portion 11 are gradually reduced along the first extension direction D1. A direction extending from the second portion 12 to the first portion 11 is referred to as a second extension direction D2. The sizes of the more than one air outlets 107 defined in the second portion 12 are gradually reduced along the second extension direction D2. Furthermore, each of the air outlets 107 is a strip-shaped air outlet. An extension direction of the strip-shaped air outlet may be inclined in a preset angle relative to the extension direction of the arc-shaped shell 10. The preset angle may be 90 degrees. It shall be understood that, by defining the air outlets 107 in the above extension direction, the air outlet of the neck fan 30 may be softer, and the user may be more comfortable, improving the user's experience. In particular, when the preset angle is 90 degrees, the air outlet efficiency of the air outlets 107 is improved. In addition, a cross-sectional area of the air duct of the first portion is gradually decreased along a direction from the first portion to the second portion; and/or a cross-sectional area of the air duct of the second portion is gradually decreased along a direction from the second portion to the first portion.

Further, the partition 13 is connected to a surface of the inner wall 101 facing the outer wall 102 and extends towards the outer wall 102. The partition 13 includes a partition body 130, a first guiding portion 131, and a second guiding portion 132. One end of the partition body 130 is connected to an end of the bottom wall 104 near the end plate 109. The other end of the partition body 130 extends towards a middle of the top wall 103 to be close to a middle of the top wall 103. The first guiding portion 131 includes a first sub-portion 131a and a second sub-portion 131b. The first sub-portion 131a surrounds a periphery of the fan assembly 20 arranged near the end plate 109. The second portion 131b is connected between the first portion 131a and the top wall 103. The second guiding portion 132 is connected to the partition body 130 and surrounds a periphery of the fan assembly 20 near the connecting portion 14. It shall be understood that, the partition body 130 is configured to divide the receiving space 105 into the two receiving sub-spaces 105a and 105b. The first guiding portion 131 and the second guiding portion 132 are configured to match shapes of the fan blade assemblies 22 so as to guide the air and achieve a better air outlet effect.

Further, an end of the second guiding portion 132 away from the partition body 130 extends to reach the connecting portion 14. Along a direction from the end plate 109 to the connecting portion 14, a distance between the second guiding portion 132 and the bottom wall 103 is gradually reduced until the second guiding portion 132 is tangent to the bottom wall 103, and then the distance between the second guiding portion 132 and the bottom wall 103 is gradually increased to a predetermined value and remains at the predetermined value. The predetermined value may be determined according to actual demands, for example, in some embodiments, the predetermined value may be a half of a distance between the top wall 103 and the bottom wall 104. Such arrangement of the second guiding portion 132 allows the air duct to extend to reach the connecting portion 14. In addition, some of the air outlets 107 are defined near the connecting portion 14. In this way, a range of the air output from the neck fan 30 is larger, improving the cooling effect.

Further, the neck fan 30 further includes an electronic control assembly 15. The electronic control assembly 15 includes a battery and a printed circuit board 151. The second guiding portion 132 and the partition body 130 cooperatively define a receiving chamber 133 to receive at least part of the electronic control assembly 15. It shall be understood, the electronic control assembly 15 are received in the receiving chamber 133, preventing heat generated by the electronic control assembly 15 from entering the receiving sub-spaces 105a and 150b, and therefore, the cooling effect may not be affected. In addition, such arrangement allows individual arrangement of heat dissipation and wiring of the electronic control assembly 15, thereby improving the usage safety.

Further, the electronic control assembly 15 further includes a switch button 152 and a data port 153. The outer wall 102 of the second portion 12 defines a first opening 102a corresponding to the switch button 152 and a second opening 102b corresponding to the data port 153. The switch button 152 is mounted corresponding to the first opening 102a and connected to the printed circuit board 151. The data port 153 is mounted corresponding to the second opening 102b and connected to the printed circuit board 151. Such arrangement allows the user to operate the neck fan easily, improving user's experience. Furthermore, it shall be understood, in addition to the electronic control assembly 15, structures and elements of the first portion 11 and the second portion 12 are symmetrically arranged to increase wearing comfort.

Further, the outer wall 102 includes a main plate 1021 and an auxiliary plate 1022. A shape and a position of the auxiliary plate 1022 correspond to those of the partition 13. The auxiliary plate 1021 is connected between the main plate 1021 and the partition 13. It shall be understood that the auxiliary plate 1022 and the partition 13 cooperatively define the air duct of the fan assembly 20, so as to achieve a better air guiding effect.

Figure 7:
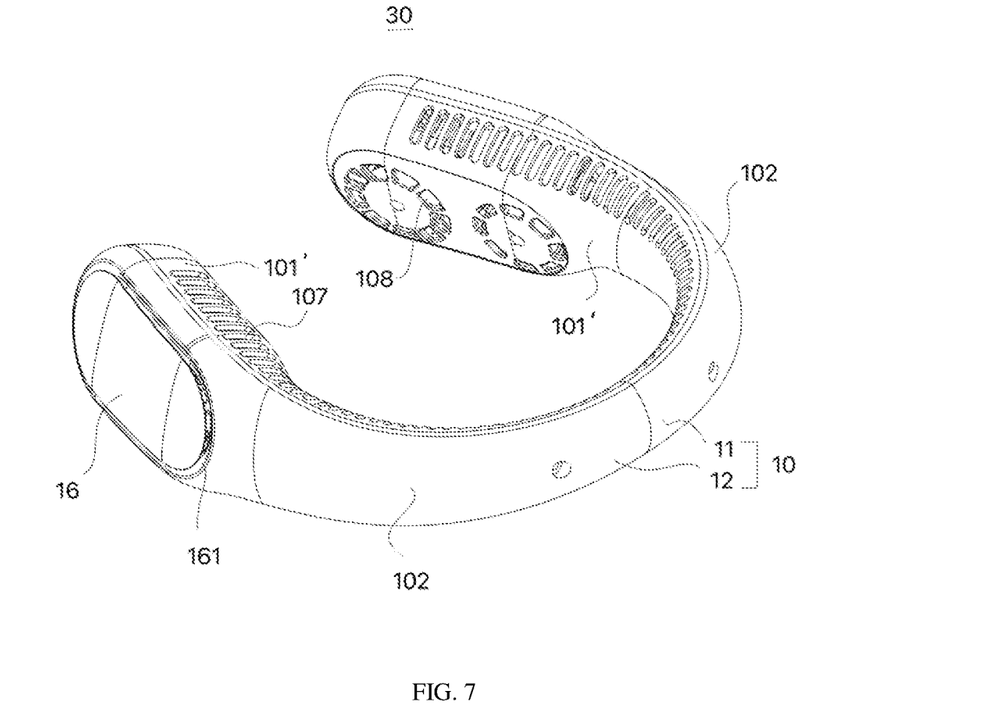
FIG. 7 is a schematic view of a neck fan in according to a second embodiment of the present disclosure.
Figure 8:
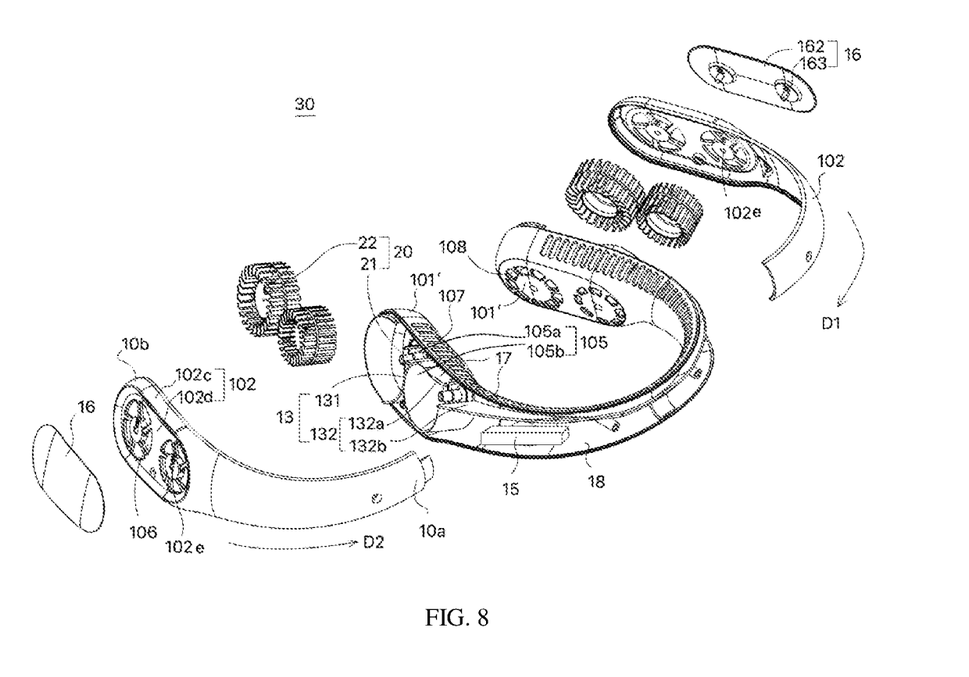
FIG. 8 is an exploded view of the neck fan of FIG. 7.

In another embodiment, as shown in FIGS. 7 and 8, FIG. 7 is a schematic view of a neck fan 30 according to an embodiment of the present disclosure, and FIG. 8 is an explosive view of the neck fan 30 of FIG. 7. The neck fan 30 includes an arc-shaped shell 10 and at least four fan assemblies 20. The at least four fan assemblies 20 are arranged inside the arc-shaped shell 10. It shall be understood that, in the present embodiment, a neck fan having four fan assemblies 20 may be taken as an example for illustration.

The arc-shaped shell 10 may be hung around the neck of the user. The arc-shaped shell 10 includes a first portion 11 and a second portion 12. The first portion 11 and the second portion 12 are arranged around two sides of the neck, such as a left side and a right side. Each of the first portion 11 and the second portion 12 includes a side wall that defines a receiving space 105. Each of the first portion 11 and the second portion 12 defines air inlets 106 and air outlets 107 communicating with the receiving space 105.

At least one partition 13 is received in the receiving space 105 to divide the receiving space 105 into at least two receiving sub-spaces 105a and 150b. The at least two receiving sub-spaces 105a and 150b are arranged successively along an extension direction of the arc-shaped shell 10. Each of the at least two receiving sub-spaces correspond to and communicate with some of the air inlets 106 and some of the air outlets 107. Each of the fan assemblies 20 is received in one corresponding receiving sub-space. Each of the fan assemblies is configured to guide the air, which flows into the corresponding receiving sub-space through corresponding air inlets 106, to flow to air outlets 107 corresponding to the receiving sub-space, allowing the air to be blown out through the corresponding air outlets 107. The number of the air outlets 107 may be more than one. The more than one air outlets 107 may be distributed along the extension direction of the arc-shaped shell 10. Sizes, shapes of the air outlets 107 and/or distances between every two adjacent air outlets 107 vary gradually along the extension direction of the arc-shaped shell 10.

Compared to the neck fan in the art, in the neck fan 30 illustrated in the above-mentioned embodiments, the arc-shaped shell 10 includes the first portion 11 and the second portion 12. The first portion 11 and the second portion 12 are configured to be around two opposite sides of the neck. Each of the first portion 11 and the second portion 12 defines the receiving space 105, the air inlets 106, and the air outlets 107. The air inlets 106 and the air outlets 107 communicate with the receiving space 105. Each receiving space 105 is divided into at least two receiving sub-spaces 105a and 105b by the partition 13. Each of the fan assemblies 20 is arranged in one of the receiving sub-spaces and configured to guide the air at the air inlets 106 to flow to the air outlets 107 to be blown out. Since the fan assemblies 20 are received in the receiving space 105, foreign matters, such as hair, may not be absorbed into the fan assemblies easily, allowing the neck fan to be used safely and conveniently. In the present embodiment, four receiving sub-spaces 105a and 105b are defined along the extension direction of the arc-shaped shell 10, and four fan assemblies 20 may be arranged and received in four receiving sub-spaces respectively. Since a plurality of the receiving sub-spaces 105a and 105b are defined, a length of the air duct in each of the receiving sub-spaces may be relatively short. When the air is flowing in each of the receiving sub-spaces, a concentration of the air being output may be reduced, the user may be comfortable about the air output, wind noise may be reduced, and an air volume loss may be reduced. The applicant of the present disclosure finds that, the longer the air duct, the longer period of time that the air flows along the receiving sub-space, increasing the wind noise and the air volume loss. By dividing the receiving space 105 into the plurality of receiving sub-spaces 105a and 105b, the wind noise and the air volume loss may be reduced significantly.

In detail, the side wall includes a first side wall 101' configured to be close to the neck of the user and a second side wall 102 opposite to the first side wall 101'. The air inlets 106 are defined in the second side wall 102, and the air outlets 107 are defined in a region of the first side wall 101' adjacent to the second side wall 102 or defined in a region of the second side wall 102 adjacent to the first side wall 101'. In the present embodiment, the air outlets 107 are defined in the region of the first side wall 101' adjacent to the second side wall 102 and are close to the user's head and face.

Further, in detail, a direction extending from the first portion 11 to the second portion 12 may be referred to as a first extension direction D1. The sizes of the more than one air outlets 107 defined in the first portion 11 are gradually reduced along the first extension direction D1. A direction extending from the second portion 12 to the first portion 11 is referred to as a second extension direction D2. The sizes of the more than one air outlets 107 defined in the second portion 12 are gradually reduced along the second extension direction D2. Furthermore, each of the air outlets 107 is a strip-shaped air outlet. An extension direction of the strip-shaped air inlet may be inclined in a preset angle relative to the extension direction of the arc-shaped shell 10. The preset angle may be 90 degrees. It shall be understood that, by defining the air outlets 107 in the above extension direction, the air outlet of the neck fan 30 may be softer, and the user may be more comfortable, improving the user's experience. In particular, when the preset angle is 90 degrees, the air outlet efficiency of the air outlets 107 is improved. In some embodiments, the air outlets 107 may be at least one of petal-shaped and heart-shaped. It shall be understood that, both the petal-shaped air outlets 107 and the heart-shaped air outlets 107 may output the air uniformly and provides better appearance for the neck fan.

Further, each fan assembly 20 includes a driving shaft 21 and a fan blade assembly 22 mounted on the driving shaft 21. The driving shaft 21 extends from the first side wall 101' towards the second side wall 102. In this way, a thickness of the arc-shaped shell 10 along a direction from the first side wall 101' to the second side wall 102 may be reduced, such that the user may be comfortable when wearing the neck fan.

It shall be understood, the air inlets 106 are defined in the second side wall 102, and the second side wall 102 faces outwardly (i.e., away from the user's neck) allowing the air to flow into the air inlets 106 easily, allowing the air to flow in smoothly. Such arrangement together with the driving shaft 21 extending along the direction from the first side wall 101' to the second side wall 102 enables the fan blade assembly 22 to direct the air from the air inlets 106 to the air outlets 107, thereby achieving a relatively high air guiding efficiency. Moreover, the air outlets 107 are defined at the first side wall 101' close to the user's head and face, such that the air may be directed out towards the user's head and face, thereby achieving better cooling effect.

The first side wall 101' defines a plurality of air inlets 108 corresponding to each fan assembly 20. The fan assembly 20 can guide the air at the air inlets 108 to the air outlets 107. Each of the plurality of air inlets 108 is arc shaped. The plurality of air inlets 108 corresponding to each fan assembly are arranged in a circular shape. It shall be understood, such arrangement provides a better appearance of the neck fan 30, and prevents the foreign matters from entering the fan assembly 20. Such arrangement together with shapes of the fan assemblies 20 achieves a better air guiding effect.

In an embodiment, the first side wall defines the plurality of air inlets 108, and the second side wall defines the plurality of air inlets 106. The first side wall faces the neck of the user, and the second side wall is connected to the first side wall and faces away from the neck. Further, at least one of a region of the first side wall close to the second side wall and a region of the second side wall close to the first side wall defines the plurality of air outlets 107. In addition, the plurality of air outlets 107 are located between the plurality of air inlets 108 of the first side wall and the plurality of air inlets 106 of the second side wall along an extension direction of the driving shaft 21.

Further, the first portion 11 has a connecting end 10a connected to the second portion 12 and a free end 10b away from the connecting end 10a; and the second portion 12 also has a connecting end 10a connected to the first portion 11 and a free end 10b away from the connecting end 10a. Sizes of the air outlets 107 corresponding to the fan assembly 20 adjacent to the connecting end 10a are less than those of the air outlets 107 corresponding to the fan assembly 20 adjacent to the free end 10b. An outer diameter of the fan blade assembly 22 adjacent to the connecting end 10a is less than that of the fan blade assembly 22 adjacent to the free end 10b. It shall be understood, the sizes of the air inlets 106 and the diameter of the fan blade assembly 22 enables a size of the arc-shaped shell 10 to be reduced gradually along a direction from the free end 10b to the connecting end 10a, such that the shape of the neck fan may fit a curve of the neck more appropriately, increasing wearing comfort.

In the present embodiment, each of the first portion 11 and the second portion 12 includes a cover 16. The cover 16 is disposed on a side of the second side wall 102 away from the first side wall 101' and corresponds to (such as covers) the air inlets 106. A gap 161 communicated with the air inlets 106 is defined between an edge of the cover 16 and the second side wall 102 to allow air to flow into the air inlets 106.

Further, the second side wall 102 includes a main body 102c and defines a recess 102d. A wall of the recess 102d is connected to the main body 102c. In other words, the side of the second side wall 102 away from the first side wall 101' is recessed inwardly towards the first side wall 101' to define the recess 102d. The air inlets 106 are defined at the recess 102d, such as defined in the bottom wall of the recess 102d. The cover 16 covers the recess 102d. The cover 16 is partially connected to the main body 102c connected to wall of the recess 102d to define the gap 161. It shall be understood, the cover 16 covers the air inlets 106, and air enters through the gap 161 and the air inlets 106. In this way, a better appearance is provided, and the foreign matters may be prevented from entering the fan assembly 20, increasing the usage safety. Defining the recess 102d further reduces an overall size of the neck fan 30 and provides the appearance aesthetics.

Further, the cover 16 includes a cover body 162 and a first mounting portion 163 arranged at a side of the cover body 162 adjacent to the second side wall 102. A side of the second side wall 102 close to the cover 16 is arranged with a second mounting portion 102e. In detail, the second mounting portion 102e may be arranged on the wall of the recess 102d and is located between the plurality of air inlets 106.

Further, the cover 16 further includes the cover body 162 and the first mounting portion 163 arranged on the cover body 162. The second mounting portion 102e is arranged on the second side wall 102 and is engaged with the first mounting portion 163. Engagement between the second mounting portion 102e and the first mounting portion 163 enables the cover 16 to be mounted (such as detachably or movably mounted) on the side of the second side wall 102 away from the first side wall 101'. It shall be understood, engagement between the first mounting portion 163 and the second mounting portion 102e enables the cover 16 to be detachably or movably mounted onto the second side wall 102, allowing the neck fan to be used or disassembled easily.

Further, the first mounting portion 163 and the second mounting portion 102e may be engaged in a first mounting state or in a second mounting state. In the first mounting state, the gap 161 is defined between the edge of the cover 16 and the second side wall 102. In the second mounting state, the edge of the cover 16 abuts against the second side wall 102 so as to cover the air inlets 106. It shall be understood, the first mounting portion 163 and the second mounting portion 102e may be engaged in the first mounting state or in the second mounting state. Therefore, in the first mounting state, the air can enter the fan assembly through the gap 161 and the air inlets 106; and in the second mounting state, the gap 161 and the air inlets 106 are covered, and dust may be prevented from entering the arc-shaped shell through the air inlets 106 when the neck fan 30 is not in use, achieving the dustproof effect.

It shall be understood, the first mounting state and the second mounting state may be switched from one to the other. In some embodiments, elastic fasteners may be configured, serving as the first mounting portion and the second mounting portion. In this way, the first mounting state and the second mounting state may be switched by pressing the cover 16 along a direction facing the second side wall 102. For example, a first press is made to switch from the first mounting state to the second mounting state, and a next press is made to switch from the second mounting state to the first mounting state. There are various structures for implementing the above-mentioned press switch control, which will not be described specifically hereinafter.

In the present embodiment, the first mounting portion 163 may be a mounting shaft connected to the cover body 162, and the second mounting portion 102e may be a mounting hole corresponding to the mounting shaft. In other embodiments, the first mounting portion 163 may be a mounting hole defined in the cover body 162, and the second mounting portion 102e may be a mounting shaft corresponding to the mounting hole. It shall be understood, the mounting shaft may be received in the mounting hole to engage the cover 16 to the second side wall 102, achieving an easy mounting operation.

In the present embodiment, the partition 13 includes a partition body 131 and a guiding portion 132. A shape of the partition body 131 at least partially fits to a shape of the fan assembly 20, and the partition body 131 surrounds a periphery of the fan assembly 20. The guiding portion 132 is connected to the partition body 131. The guiding portion 132 and the side wall cooperatively define the air duct communicated to the air outlets 107. It shall be understood that by adapting the partition part 131 to the shape of the fan assembly 20 and by configuring the guiding portion 132 and the side wall to cooperatively define the air duct 17 communicated to the air outlets 107, a better air guiding effect may be achieved, and an air inlet and outlet efficiency may be improved.

Further, for each of the first portion 11 and the second portion 12, the guiding portion 132 includes a first guiding sub-portion 132a located between two fan assemblies 20 and a second guiding sub-portion 132b arranged at a side of one of the two fan assemblies 20 away from the other of the two fan assemblies. The second guiding sub-part 132b extends from one of the first portion 11 and the second portion 12 to the other of the first portion 11 and the second portion 12. A side of the second guiding sub-portion 132b and the side wall cooperatively define an accommodating space 18. The neck fan 30 further includes an electronic control assembly 15. The electronic control assembly 15 includes a battery and a printed circuit board. The accommodating space 18 is defined to receive at least one of the battery and the printed circuit board. It shall be understood, by receiving the electronic control assembly 15 in the accommodating space 18, configuration of the neck fan 30 may be effectively balanced, providing wearing comfort for the user. In addition, the fan blade assembly 20 may be a turbine fan blade assembly. It shall be understood that the turbine fan blade assembly may achieve lower noise and higher safety.

In an embodiment, as shown in FIG. 4, the present disclosure provides a turbine blade assembly 22 for a neck fan. The turbine blade assembly 22 has a first side and a second side opposite to the first side. The turbine blade assembly 22 includes a first side blade disposed at the first side, a second side blade disposed at the second side, and a separation plate disposed between the first side and the second side. The first side defines a first inlet window, and the second side defines a second inlet window. The first inlet window and the second inlet window are defined to allow air to flow in from an outside of the neck fan. A bottom wall of the first inlet window is recessed from a plane where the first side blade is disposed. A bottom wall of the second inlet window is recessed from a plane where the second side blade is disposed.

The above description only describes embodiments of the present disclosure, and is not intended to limit the present disclosure, various modifications and changes can be made to the present disclosure. Any modifications, equivalent substitutions, improvements, etc. made within the spirit and scope of the present disclosure are intended to be included within the scope of the present disclosure.

The invention claimed is:

1. A neck fan, comprising:
an arc-shaped shell, configured to be worn around a neck of a user,
wherein the arc-shaped shell comprises a first portion configured to be worn around a side of the neck and a second portion configured to be worn around another side of the neck;
each of the first portion and the second portion comprises a wall defining a receiving space, and the wall comprises a first side wall close to the neck and a second side wall connected to and opposite to the first side wall; and
each of the first side wall and the second side wall defines a plurality of air inlets, at least one of the first side wall and the second side wall defines a plurality of air outlets, and the plurality of air inlets and the plurality of air outlets are communicating with the receiving space;
a plurality of fan assemblies, wherein each of the receiving space of the first portion and the receiving space of the second portion receives one of the plurality of fan assemblies, wherein each of the plurality of fan assemblies is configured to guide air from the plurality of air inlets of the first side wall and the second side wall of a respective portion to the plurality of air outlets of the respective portion,
wherein one of the plurality of fan assemblies corresponds to at least one of the plurality of air inlets in the first side wall and at least one of the plurality of air inlets in the second side wall, and the at least one of the plurality of air inlets in the first side wall and at least one of the plurality of air inlets in the second side wall, which correspond to the same one of the plurality of fan assemblies, face opposite directions.

2. The neck fan according to claim 1, further comprising at least one partition, received in the receiving space and dividing the receiving space into at least two receiving sub-spaces;
wherein each of the plurality of fan assemblies is received in one of the at least two receiving sub-spaces, and each of the plurality of fan assemblies is configured to guide air from the plurality of air inlets of a respective receiving sub-space to the plurality of air outlets of the respective receiving sub-space.

3. The neck fan according to claim 2, further comprising an electronic control assembly, which comprises a battery and a printed circuit board;
wherein each of the at least one partition comprises a partition body, a first guiding portion, and a second guiding portion; and
the partition body and the second guiding portion cooperatively define a receiving chamber, and at least a part of the electronic control assembly is received in the receiving chamber.

4. The neck fan according to claim 3, wherein,
the battery of the electronic control assembly is at least partially received in the receiving chamber; or
the printed circuit board of the electronic control assembly is at least partially received in the receiving chamber; or
the battery of the electronic control assembly is disposed at a position between the first portion and second portion; or
the battery and the printed circuit board of the electronic control assembly are both received in the receiving chamber.

5. The neck fan according to claim 1, wherein,
each of the first portion and the second portion comprises a cover;
the cover is disposed on a side of the second side wall away from the first side wall and corresponds to the plurality of air inlets; and
a gap is defined between an edge of the cover and the second side wall and is communicated with the plurality of air inlets.

6. The neck fan according to claim 1, wherein,
each of the plurality of fan assemblies comprises a driving shaft and a fan blade assembly mounted on the driving shaft; and
the driving shaft extends from the first side wall towards the second side wall.

7. The neck fan according to claim 1, wherein the fan blade assembly is a turbine blade assembly; and
the turbine blade assembly includes a turbine fan, and the turbine fan defines two inlet windows corresponding to the air inlets of the first side wall and the second side wall respectively.

8. The neck fan according to claim 6, wherein the plurality of air outlets are defined in the first side wall, and the plurality of air outlets are located between the plurality of air inlets in the first side wall and the plurality of air inlets in the second side wall along an extending direction of the driving shaft.

9. The neck fan according to claim 1,
wherein the plurality of air outlets are distributed along an extension direction of the arc-shaped shell; and
at least one of sizes, shapes and distances between every two adjacent air outlets of the plurality of air outlets vary along the extension direction of the arc-shaped shell in a predetermined manner.

10. The neck fan according to claim 9, wherein
the extension direction comprises a first extension direction and a second extension direction;
the first extension direction is a direction extending from the first portion to the second portion, and the sizes of the plurality of air outlets defined in the first portion are reduced along the first extension direction; and the second extension direction is a direction extending from the second portion to the first portion, and the sizes of the plurality of air outlets defined in the second portion are reduced along the second extension direction.

11. A neck fan, comprising:

an arc-shaped shell, configured to be worn around a neck of a user,
  wherein the arc-shaped shell comprises a first portion configured to be worn around a side of the neck and a second portion configured to be worn around another side of the neck;
  each of the first portion and the second portion comprises a wall, the wall defines a receiving space, a plurality of air inlets communicating with the receiving space, and a plurality of air outlets communicating with the receiving space;
a partition, received in the receiving space and dividing the receiving space into two receiving sub-spaces, wherein the two receiving sub-spaces are distributed along an extension direction of the arc-shaped shell; and
a plurality of fan assemblies, wherein one of the two receiving sub-spaces receives one of the plurality of fan assemblies, and the plurality of fan assemblies are configured to guide air to flow from the plurality of air inlets to the plurality of air outlets; and
a plate;
  wherein the partition in the receiving space of the first portion, the wall of the first portion, and the plate cooperatively define a first air duct, the partition in the receiving space of the second portion, the wall of the second portion, and the plate cooperatively define a second air duct, the first air duct is dis-communicated with the second air duct by the plate; and
  a cross-sectional area of the first air duct of the first portion is decreased along a direction from the plurality of air inlets of the first portion to the plate, and/or
  a cross-sectional area of the second air duct of the second portion is decreased along a direction from the plurality of air inlets of the second portion to the plate.

12. The neck fan according to claim 11,
wherein the plurality of air outlets are distributed along an extension direction of the arc-shaped shell; and
at least one of sizes, shapes and distances between every two adjacent air outlets of the plurality of air outlets vary along the extension direction of the arc-shaped shell in a predetermined manner.

13. The neck fan according to claim 12,
wherein the extension direction comprises a first extension direction and a second extension direction;
the first extension direction is the direction from the first portion to the second portion, and the sizes of the plurality of air outlets defined in the wall of the first portion are reduced along the first extension direction; and
the second extension direction is a direction from the second portion to the first portion, and the sizes of the plurality of air outlets defined in the wall of the second portion are reduced along the second extension direction.

14. The neck fan according to claim 11,
wherein each of the plurality of air outlets is a strip-shaped air outlet; and
an extension direction of the strip-shaped air outlet is inclined in a preset angle relative to the extension direction of the arc-shaped shell.

15. The neck fan according to claim 11,
wherein the first portion has a connecting end connected to the second portion and a free end away from the connecting end;
the second portion has another connecting end connected to the first portion and another free end away from the another connecting end;
each of the plurality of fan assemblies comprises a fan blade configured to rotate to generate an air flow, an outer diameter of the fan blade adjacent to the connecting end is less than that of the fan blade adjacent to the free end, and an outer diameter of the fan blade adjacent to the another connecting end is less than that of the fan blade adjacent to the another free end.

16. The neck fan according to claim 11,
wherein the first portion has a connecting end connected to the second portion and a free end away from the connecting end;
the second portion has another connecting end connected to the first portion and another free end away from the another connecting end;
a size of the first portion is reduced along a direction from the free end to the connecting end; and
a size of the second portion is reduced along a direction from the another free end to the another connecting end.

17. The neck fan according to claim 11,
wherein the wall comprises a first side wall close to the neck and a second side wall opposite to and connected to the first side wall to define the receiving space;
each of a side of the first side wall facing the neck and a side of the second side wall facing away from the neck defines the plurality of air inlets; and
the plurality of fan assemblies are configured to direct air from the plurality of air inlets of the respective receiving sub-spaces to the plurality of air outlets of the respective receiving sub-spaces.

18. A turbine blade assembly for a neck fan,
wherein turbine blade assembly has a first side and a second side opposite to the first side, when the neck fan is worn to a user, the first side faces towards a neck of the user, and the second side faces away from the neck of the user;
the turbine blade assembly comprises a first side blade, which is disposed at the first side and faces towards the neck of the user when the neck fan is worn to the user, a second side blade, which is disposed at the second side and faces away from the neck of the user when the neck fan is worn to the user;
the first side defines a first inlet window, the second side defines a second inlet window; and
the first inlet window and the second inlet window are defined to face opposite directions and to allow air to flow in from an outside of the neck fan,
wherein the turbine blade assembly further comprises an air outlet port;
the first inlet window and the second inlet window, which face opposite directions, are configured to guide air from the outside of the neck fan to the same air outlet port, and the air outlet port is configured to output the intake air to an inside of the neck fan.

19. The turbine blade assembly according to claim 18, wherein a bottom wall of the first inlet window is recessed from a plane where the first side blade is disposed; and a bottom wall of the second inlet window is recessed from a plane where the second side blade is disposed.

* * * * *